United States Patent [19]

Halderson

[11] 4,134,399
[45] Jan. 16, 1979

[54] SKIN PROTECTIVE DEVICE

[76] Inventor: Alfred Halderson, Rte. 1, Valders, Wis. 54245

[21] Appl. No.: 806,152

[22] Filed: Jun. 13, 1977

[51] Int. Cl.² ............................................. A61F 13/00
[52] U.S. Cl. ................................................ 128/132 R
[58] Field of Search ..................... 128/132 R, 153, 154

[56] References Cited

U.S. PATENT DOCUMENTS 4,000,737  1/1977  Horn .................................... 128/154

FOREIGN PATENT DOCUMENTS 515236  12/1930  Fed. Rep. of Germany ........... 128/154
1104098  11/1955  France ..................................... 128/154
1146313  11/1957  France ..................................... 128/154

Primary Examiner—John D. Yasko
Attorney, Agent, or Firm—Michael, Best & Friedrich

[57] ABSTRACT

The skin protective device, which can be positioned adjacent a wound or sensitive skin area and serve as a protective shield against contact by foreign objects or as a support for maintaining a bandage out of contact with the wound or sensitive skin area, includes a plurality of longitudinally spaced, generally U-shaped support elements. Each of the support elements include an elongated, laterally extending central portions of sufficient length to bridge or span the wound or sensitive skin area and a pair of support legs which depend from the opposite ends of the central portion and are adapted to rest on healthy skin surrounding the wound or sensitive skin area. Adjacent pairs of the support elements are connected together by one or more relatively narrow connecting links made from a flexible and severable material so that a device, including two or more of the support elements, can be conveniently conformed to the natural contour of the body and cut in a length appropriate for the particular wound or sensitive skin area involved.

The support elements and connecting link(s) preferably are from the same material, such as a flexible transparent synthetic thermoplastic material, and as a one-piece unit.

8 Claims, 4 Drawing Figures

U.S. Patent  Jan. 16, 1979  4,134,399
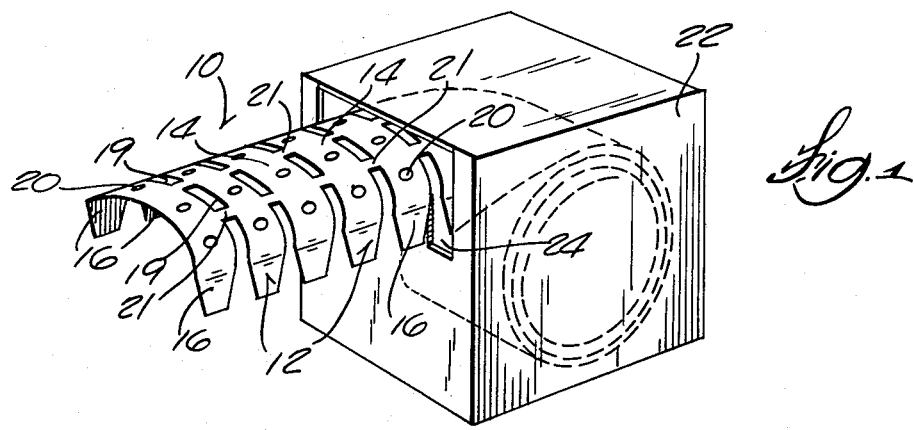
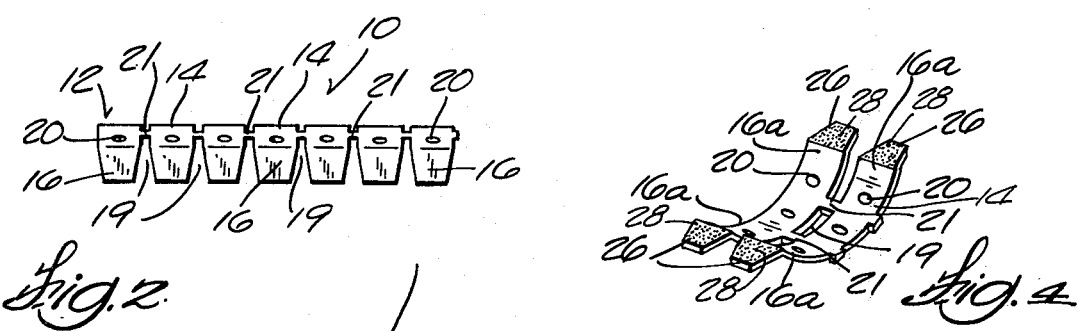
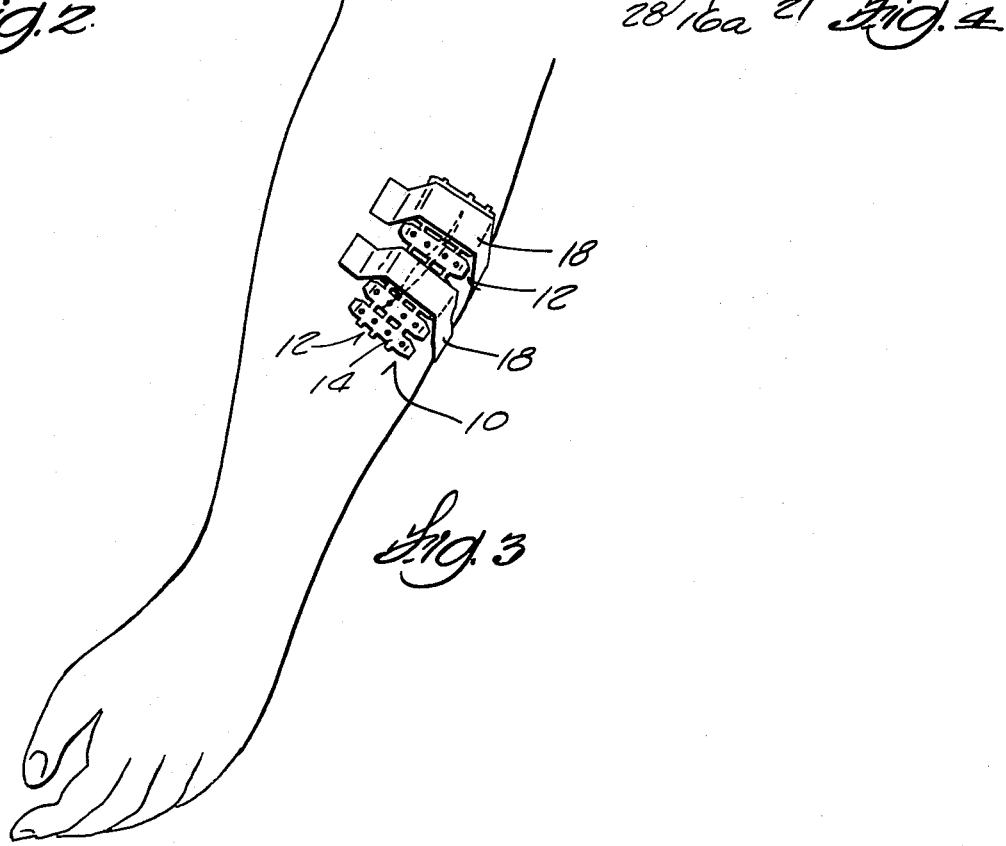

SKIN PROTECTIVE DEVICE

BACKGROUND OF THE INVENTION

This invention relates to skin protective devices and, more particularly, to skin protective devices which can be positioned adjacent wounds, burns, cuts, sores or other sensitive areas of skin and serve as a protective shield or as a support for maintaining a bandage out of contact with a wound or sensitive skin area.

Small skin abrasions or other minor skin wounds usually are protected from clothing and other foreign objects by adhesive bandages or gauzes. This type of protection usually cannot be used effectively for many more serious skin wounds, such as severe abrasions, burns, surgical incisions, skin grafts and the like, particularly for larger size wounds. In addition to the potential problem of the bandage or gauze sticking to the open wound or scab, such wounds often require a free circulation of air for rapid healing as well as protection from foreign objects, such as clothing, bed linens, and the like.

Various devices have been developed for protecting skin wounds, particularly surgical wounds. However, such prior art devices usually are quite complicated, are not arranged so they can be conveniently sized for the particular wound or sensitive skin area involved, and/or do not have the capability of being conveniently conformed to the natural contour of the body in the area of the wound. Examples of prior art protective devices are disclosed in the following U.S. Pat. Nos.: Sene 2,443,481 issued June 15, 1948; Perkins 3,304,938 issued Feb. 21, 1967; McCartney 3,976,066 issued Aug. 24, 1976; Horn 4,000,737 issued Jan. 4, 1977.

SUMMARY OF THE INVENTION

A principal object of the invention is to provide a simple, inexpensive skin protective device which can be positioned adjacent a wound or sensitive skin area for protecting same from being contacted by foreign objects, which can be conveniently conformed to the contour of the area of the body adjacent the wound, and which, after application on the body, will flex with natural body movement.

Another principal object of the invention is to provide such a skin protective device which permits air to freely circulate over the wound or sensitive skin area.

A further principal object of the invention is to provide such a skin protective device which can be conveniently dispensed and sized for the particular wound or sensitive skin area involved.

A still further principal object of the invention is to provide such a skin protective device which can be used as is for shielding a wound or sensitive skin area or can be used for supporting a bandage out of contact with the wound or sensitive skin area.

Other objects and advantages of the invention will become apparent to those skilled in the art upon reviewing the following detailed description, the drawing and the appended claims.

The skin protective device provided by the invention includes a plurality of longitudinally spaced, generally U-shaped support elements, each having an elongated, laterally extending raised central portion of sufficient length to span a wound or sensitive skin area and a pair of support legs which depend from the opposite ends of the central portion and are adapted to rest on the skin at locations beyond the wound or sensitive skin area for supporting the central portion thereabove. Adjacent pairs of the support elements are connected together by one or more connecting links made from a flexible and severable material. The flexible character of the connecting link(s) permit the support elements to be flexed and twisted relative to each other, thereby permitting the device to be conveniently conformed to the natural contour of the body in the area of the wound or sensitive skin area and permitting the device to flex with natural body movement after installation. The device can be conveniently sized to the appropriate length for the particular wound or sensitive skin area involved by simply severing or cutting the appropriate connecting link(s).

In a preferred embodiment, a pair of laterally spaced connecting links are provided for connecting together the central portions of each adjacent pair of support elements at a generally central location. The support elements and connecting link(s) preferably are formed from the same material and as a one-piece unit.

In one embodiment, each support element is provided with hold down tabs which extend outwardly and integrally from the distal ends of the support legs and have a surface adapted to lie on the skin surface. In this embodiment, the device can be secured in place by strips of adhesive tape placed over the hold down tabs and secured to the skin or by coating the hold down tab surfaces with an adhesive material adapted for securing the device to the skin.

BRIEF DESCRIPTION OF THE DRAWING

FIG. 1 is a perspective view of a skin protective device embodying various of the features of the invention, shown in a dispenser container.

FIG. 2 is a side view of an elongated, severed section of the skin protective device shown in FIG. 1.

FIG. 3 illustrates a section of the skin protective device shown in FIG. 1 taped in place over and above an incision on a patient's arm.

FIG. 4 is an inverted perspective view of an alternate construction for the skin protective device which is particularly adaptable for use as a protective shield.

DESCRIPTION OF THE PREFERRED EMBODIMENTS

Illustrated in FIGS. 1–3 is a skin protective device 10 embodying various of the features of the invention. Referring to FIGS. 1 and 2, the skin protective device 10 comprises a plurality of longitudinally spaced, generally U-shaped support elements 12 each including an elongated, laterally extending raised central portion 14 having a length sufficient to bridge or span the particular skin wound or sensitive skin area involved, such as a burn, cut, abrasion, surgical incision, skin graft or the like.

Depending generally perpendicularly from the opposite ends of the central portion 14 of each support element 12 is a pair of support legs 16 which are adapted to rest on the skin at locations beyond the wound or sensitive skin area for supporting the central portion 14 above and out of contact with the wound or sensitive skin area as shown in FIG. 3. Thus, the support legs 16 straddle the wound or sensitive skin area and cooperate with the central portion 14 to prevent clothing, bed linens and other foriegn objects from contacting and/or rubbing against the wound or sensitive skin area and to permit air to circulate freely over and around the wound or sensitive skin area. When the skin protective device is secured to the skin with strips of adhesive tape 18 as shown in FIG. 3, air can circulate through the spacings 19 between the support elements 12 and through the open opposite ends of the protective device 10. To further enhance circulation of air, each of the support elements 12 preferably is provided with a plurality of laterally spaced ventilating ports or holes 20.

The support elements 12 are connected together by one or more relatively narrow connecting links 21 made from a flexible material which can be conveniently severed or cut by a pair of scissors or the like. The flexible character of the link(s) 21 permits the support elements 12 to be flexed and/or twisted relative to each other so that the resulting protective skin device 10, including two or more of the support elements 12, can be conveniently conformed to the natural contour of the body in the area adjacent the wound or sensitive area as shown in FIG. 3.

While the skin protective device 10 can be fabricated and marketed in a variety of lengths most suitable for various common skin wounds or surgical incisions, the flexible character of the connecting link(s) 21 permits the device to be conveniently stored as a roll in a suitable dispenser container 22 as shown in FIG. 1. The lower end portion of the support legs 16 preferably are tapered as shown to facilitate roll up of the skin protective device 10.

The dispenser container 22 can be placed on a shelf in a doctor's office, in a hospital surgery or emergency treatment room, or in a home medicine cabinet. When dispensed in this peferred manner, an appropriate number of support elements 12, corresponding to the desired length of the protective device for the particular wound or sensitive skin area involved, is pulled from the dispenser container 22 by the doctor, nurse or patient and the link(s) 21 between the appropriate support elements 12 is cut with a pair of scissors or the like. One or both lateral margins of an outlet slot 24 in the dispenser container through which the free end of the skin protective device 10 is pulled can be provided with a knife edge (not shown) for this purpose.

To facilitate the desired flexing and convenience for cutting into appropriate lengths, and yet provide adequate structural integrity and external protection against the ingress of foreign objects, a pair of laterally spaced connecting links 21 generally centrally located and connecting the central portions 14 of adjacent pairs of the support elements 12, preferably are provided as illustrated.

The support elements 12 and the connecting links 21 preferably are formed from the same flexible material and as a one-piece unit with the support elements 12 and the connecting links 21 having a substantially uniform thickness. The skin protective device 10 can be fabricated with conventional fabrication techniques from various relatively flexible materials which can be sterilized, such as by stamping a thin strip of pliable metal, injection molding a flexible synthetic thermoplastic material, or compression molding a flexible thermosetting plastic material. In order to facilitate observing the progress of healing without removing the protective device, it is preferably made from a transparent material, most preferably from transparent flexible synthetic thermoplastic material, such as polyethylene or the like. When made from such inexpensive materials, the skin protective device 10 can be discarded after use; however, it can be sterilized and reused if desired.

A skin protective device 10 arranged in the manner illustrated in FIGS. 1-3 can be held in place on the patient's body by one or more strips of adhesive tape 18 extending over the device with the outer end portions thereof secured to the healthy skin surrounding the wound or sensitive skin area as shown in FIG. 3. The flexible character of the connecting links 21 permit the protective device 10 to move or flex with natural movement of the body.

For infected wounds where there might be fluids which could drain from the open ends and through the openings 19 between the support elements 12, an absorbent material, such as cotton or gauze, can be packed around the periphery of the device and secured in place by adhesive tape before applying the outer strips of adhesive tape 18 for holding the device in place.

In the alternate embodiment illustrated in FIG. 4, each of the support element legs 16a is provided with a hold down tab 26 which extends outwardly from and generally perpendicularly to the distal end thereof and includes a surface adapted to lie on the skin surface. If the skin protective device 10 is used primarily as a protective shield and maximum circulation of air is desired for rapid healing, such as for a surgical incision, the device can be held in place by longitudinally extending strips of adhesive which are adhesively fastened over the hold down tabs 26 and attached to the skin. If desired, the skin-engaging surface of the hold down tabs 26 can be coated with a suitable adhesive material 28 adapted to adhere to the skin surface as shown, in which case the skin protective device 10 can be used as is without any further securing means.

In order to preserve the adhesive character of the adhesive material 28 and to prevent the hold down tabs 26 from sticking together, particularly when the device is dispensed as a roll, the adhesive material 28, when used, preferably is covered with a suitable membrane (not shown) which is removed just prior to placement of the device over the wound or sensitive skin area.

While preferred embodiments of the invention have been illustrated and described in detail, it should be understood that numerous variations and modifications can be made thereto without departing from the spirit and scope of the invention. For instance, the protective device can be adapted for use on animals as well as human beings.

I claim:

1. A skin protective device adapted to be positioned adjacent a wound or sensitive skin area for protecting same against contact by foreign objects, said device comprising a one-piece unit including a plurality of longitudinally spaced, generally U-shaped support elements, each including an elongated, laterally extending, raised central portion of sufficient length to span the wound or sensitive skin area and a pair of support legs which depend from the opposite ends of said central portion and are adapted to rest on the skin at locations beyond the wound or sensitive skin area for supporting said central portion thereabove, and a pair of laterally spaced, longitudinally extending, and severable links connecting together the central portions of each adjacent pair of said support elements in closely spaced relationship, said connecting links having a width substantially less than the width of said support elements and having sufficient flexibility to permit flexing of said support elements relative to each other, thereby facilitating conformation of said device to the contour of the user's body in the vicinity of the wound or the sensitive area.

2. A skin protective device according to claim 1 wherein said support elements and said connecting links have a substantially uniform thickness.

3. A skin protective device according to claim 1 wherein said support elements include a plurality of ventilating holes.

4. A skin protective device according to claim 2 wherein said material is transparent.

5. A skin protective device according to claim 2 wherein said material is a synthetic thermoplastic material.

6. A skin protective device according to claim 4 wherein said transparent material is a synthetic thermoplastic material.

7. A skin protective device according to claim 1 including a hold down tab extending outwardly and integrally from the distal end of each of said support element legs and having a surface adapted to lie on the skin surface.

8. A skin protective device according to claim 7 including an adhesive material disposed on each of said hold down tab surfaces for securing said device to the skin.

* * * * *